(12) United States Patent
Ceric et al.

(10) Patent No.: US 11,155,545 B2
(45) Date of Patent: Oct. 26, 2021

(54) RIBOCICLIB SALTS AND SOLID STATE FORMS THEREOF

(71) Applicant: Sicor—Societa Italiana Corticosteroidi s.r.l., Milan (IT)

(72) Inventors: Helena Ceric, Zagreb (HR); Elisa Vergani, Novara (IT); Paolo S. Tiseni, Bresso (IT); Hana Kantor, Ostrava (CZ); Piero Paravidino, Sedriano (IT); Nikolina Janton, Jakovlje (HR); Christian Galluzzo, Novara (IT); Alexandr Jegorov, Dobra Voda (CZ)

(73) Assignee: Sicor—Societa Italiana Corticosteroid s.r.l., Milan (IT)

( * ) Notice: Subject to any disclaimer, the term of this patent is extended or adjusted under 35 U.S.C. 154(b) by 64 days.

(21) Appl. No.: 16/641,390

(22) PCT Filed: Aug. 22, 2018

(86) PCT No.: PCT/US2018/047434
§ 371 (c)(1),
(2) Date: Feb. 24, 2020

(87) PCT Pub. No.: WO2019/040567
PCT Pub. Date: Feb. 28, 2019

(65) Prior Publication Data
US 2020/0190084 A1 Jun. 18, 2020

Related U.S. Application Data

(60) Provisional application No. 62/593,319, filed on Dec. 1, 2017, provisional application No. 62/577,446, filed on Oct. 26, 2017, provisional application No. 62/555,170, filed on Sep. 7, 2017, provisional application No. 62/550,208, filed on Aug. 25, 2017.

(51) Int. Cl.
*C07D 471/04* (2006.01)

(52) U.S. Cl.
CPC ........ *C07D 471/04* (2013.01); *C07B 2200/13* (2013.01)

(58) Field of Classification Search
CPC combination set(s) only.
See application file for complete search history.

(56) References Cited

U.S. PATENT DOCUMENTS

| 9,193,732 B2 | 11/2015 | Calienni et al. |
| 10,336,763 B1 * | 7/2019 | Kamani ............... C07D 487/04 |
| 2017/0342075 A1 | 11/2017 | Chen et al. |

FOREIGN PATENT DOCUMENTS

WO 2016091221 A1 6/2016

OTHER PUBLICATIONS

Notification Concerning Transmittal of International Preliminary Report on Patentability issued in corresponding Appl. No. PCT/US2018/047434 dated Mar. 5, 2020 (9 pages).
International Search Report and Written Opinion of the International Searching Authority issued in corresponding Appl. No. PCT/US18/47434 dated Oct. 16, 2018 (14 pages).

* cited by examiner

*Primary Examiner* — Heidi Reese
(74) *Attorney, Agent, or Firm* — Carter, DeLuca & Farrell LLP

(57) ABSTRACT

The present disclosure relates to Ribociclib solid state forms, Ribociclib salts including Ribociclib succinate and solid state forms thereof, as well as processes for preparation thereof and pharmaceutical compositions thereof.

19 Claims, 13 Drawing Sheets

Figure 1: an X-ray powder diffraction (XRPD) pattern of Form II of Ribociclib succinate.
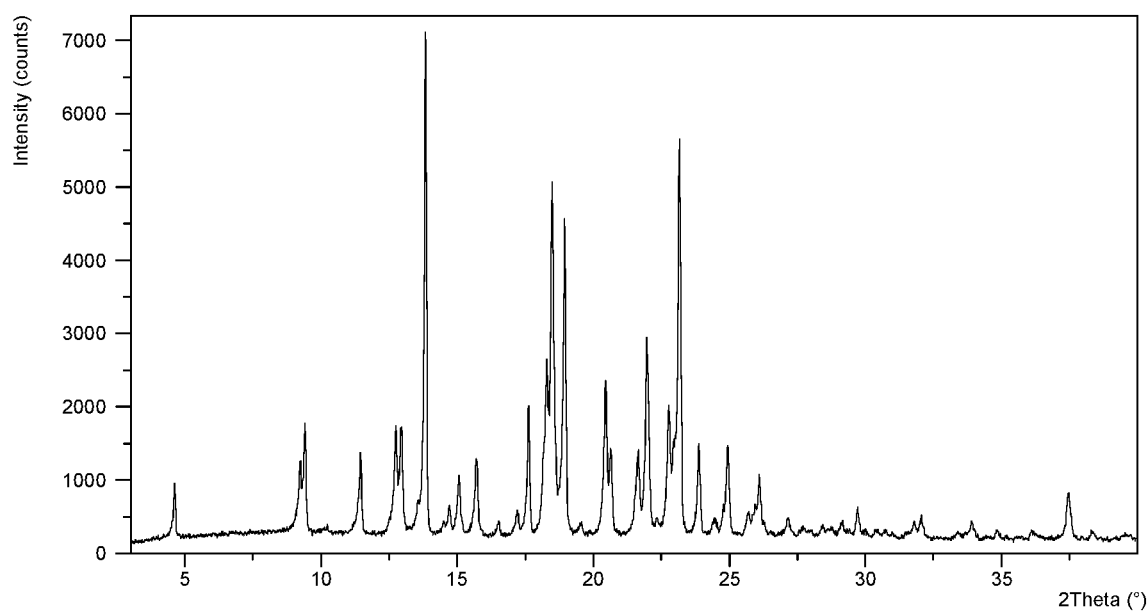

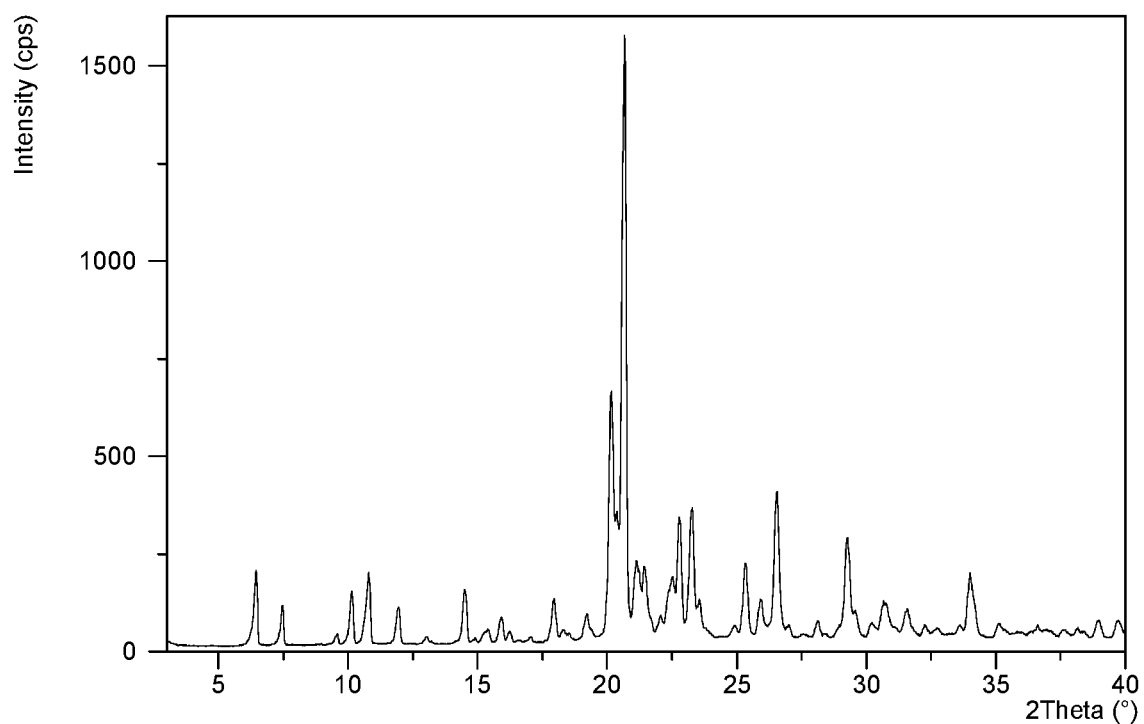
Figure 2: an X-ray powder diffraction (XRPD) pattern of Form B of Ribociclib succinate.

Figure 3: an X-ray powder diffraction (XRPD) pattern of Form C of Ribociclib succinate.
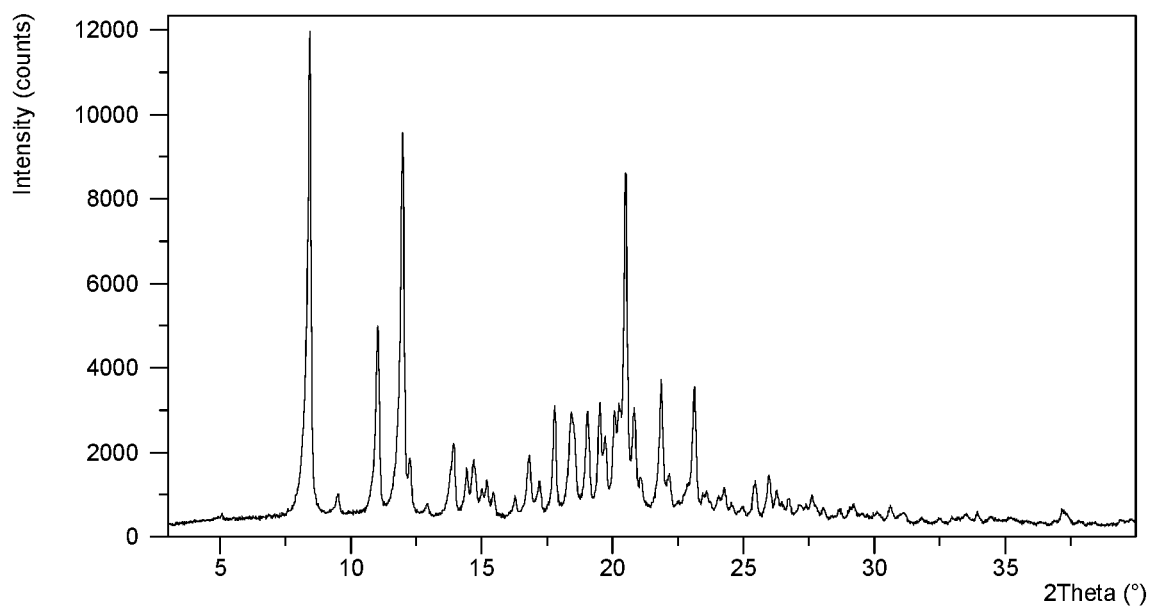

Figure 4: an X-ray powder diffraction (XRPD) pattern obtained by procedure B of example 3.
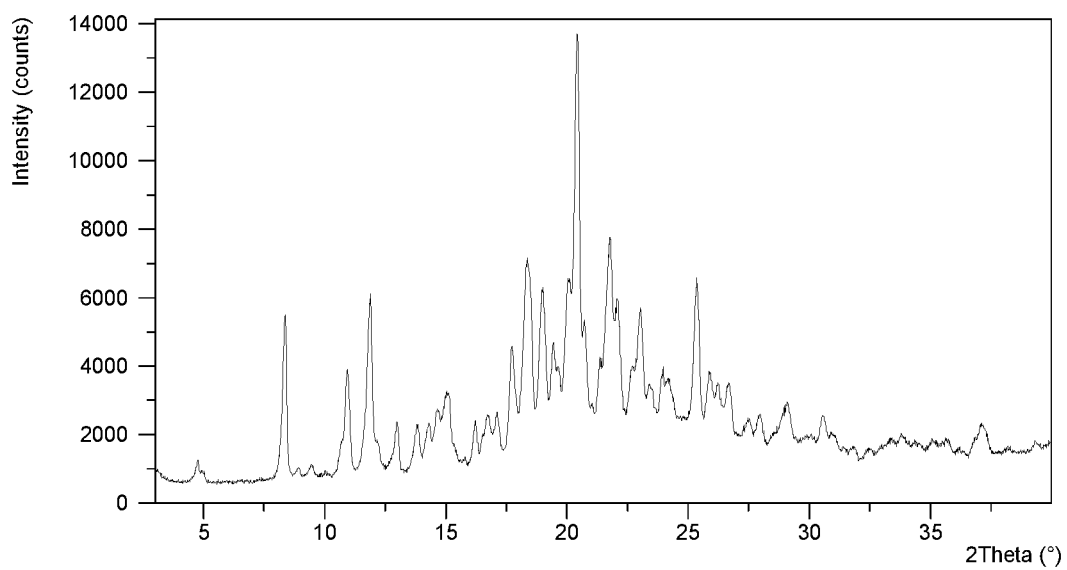

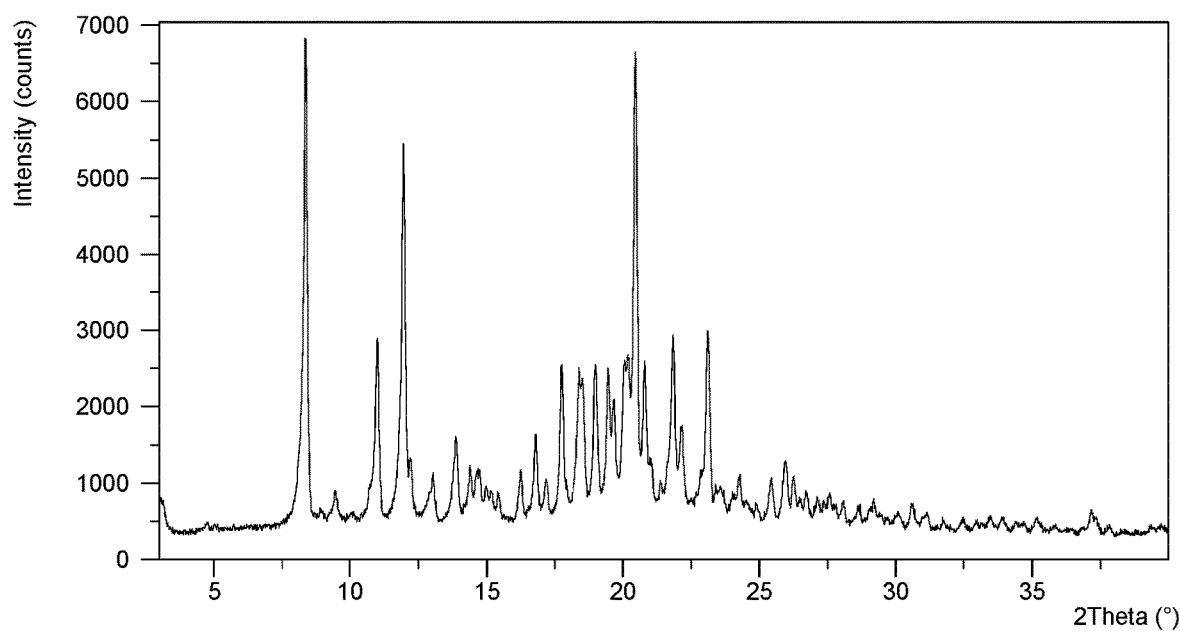
Figure 5: an X-ray powder diffraction (XRPD) pattern obtained by procedure C of example 3.

Figure 6. an X-ray powder diffraction (XRPD) pattern of Ribociclib succinate obtained by reference example 1.
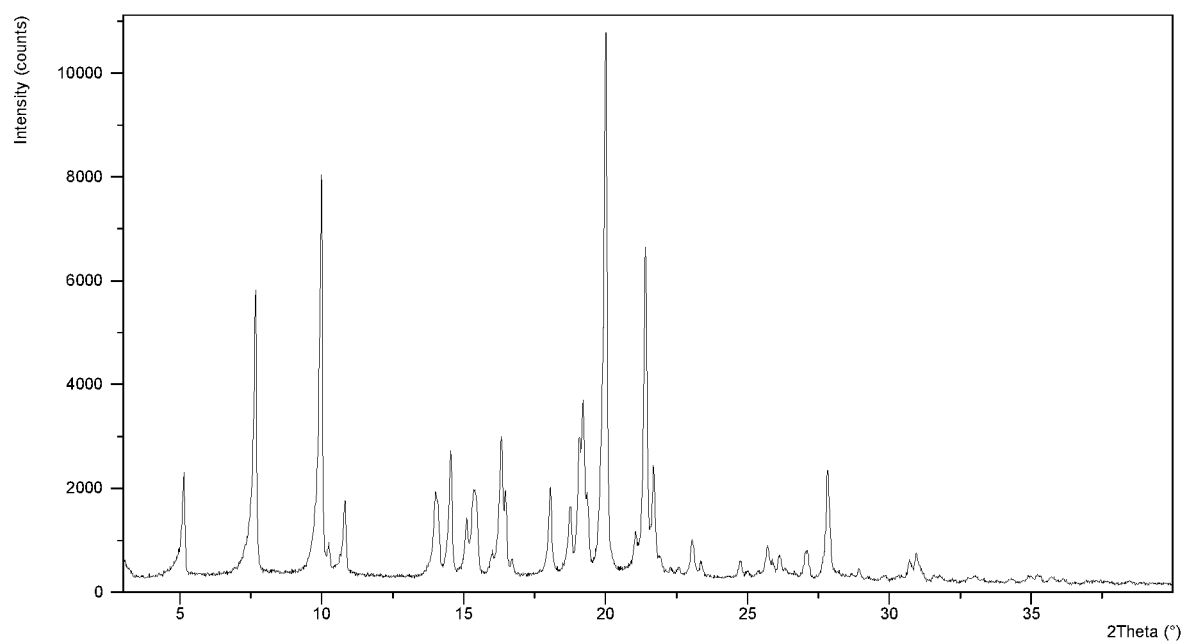

Figure 7: an X-ray powder diffraction (XRPD) pattern of amorphous Ribociclib succinate.
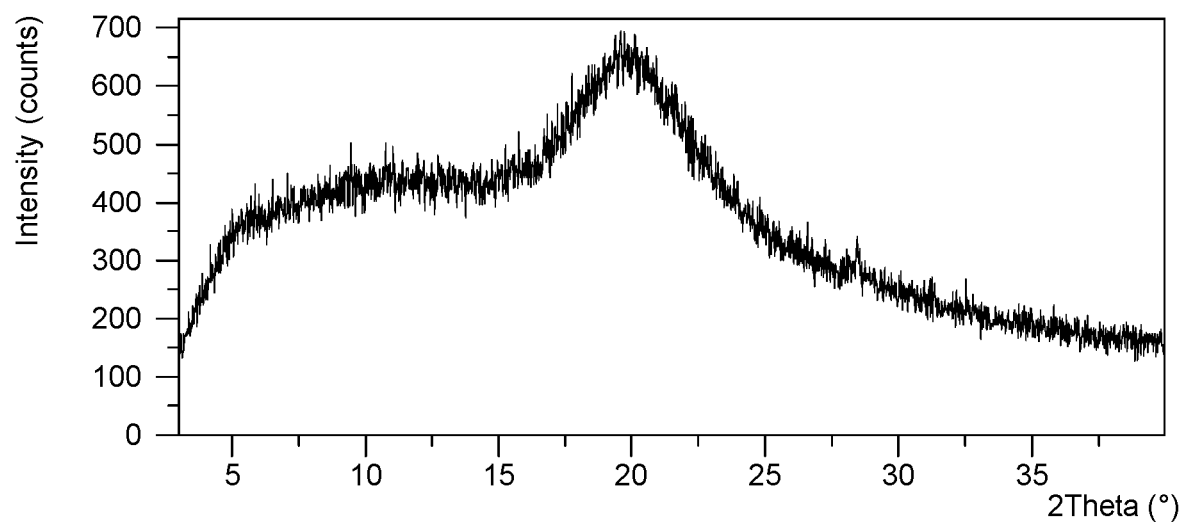

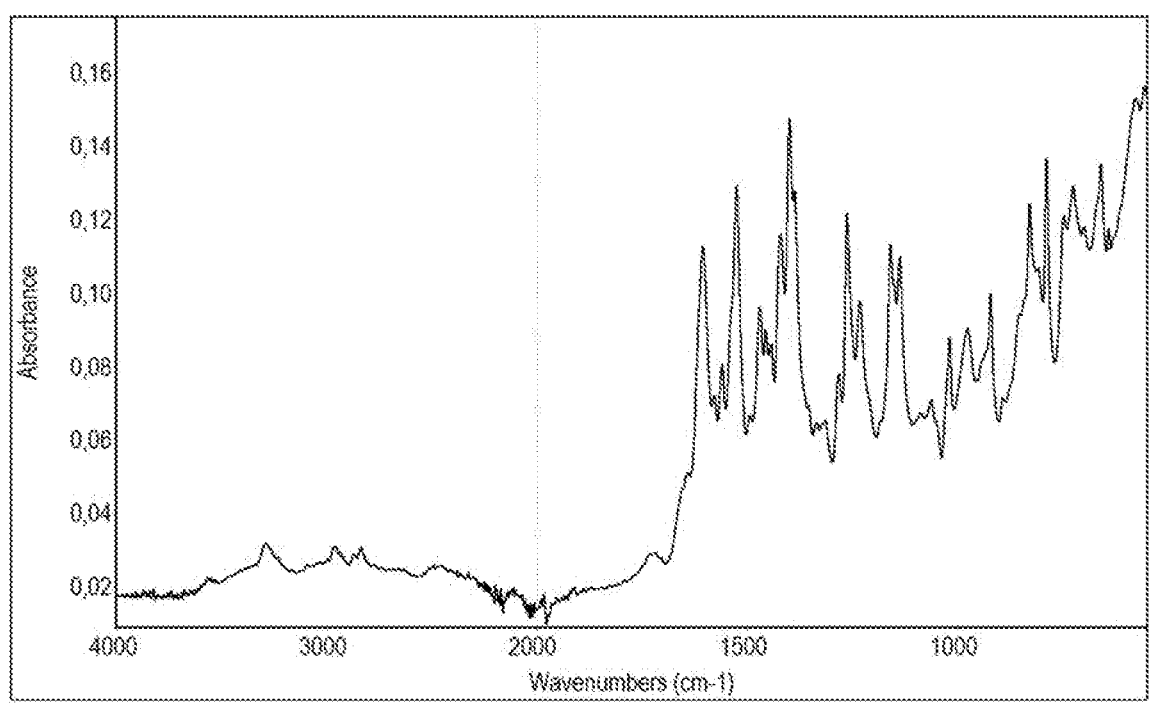
Figure 8: an FTIR spectrum of form B of Ribociclib succinate (full range)

Figure 9: an FTIR spectrum of form B of Ribociclib succinate (1800-550 cm$^{-1}$)
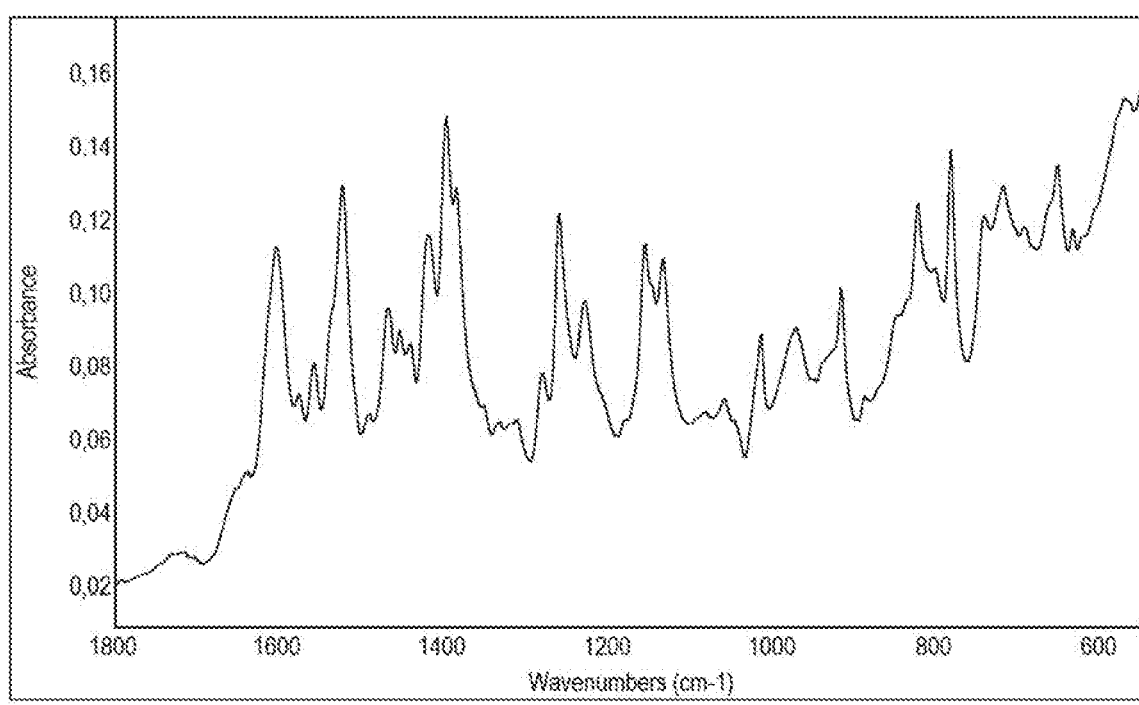

Figure 10: an FTIR spectrum of form C of Ribociclib succinate (full range)
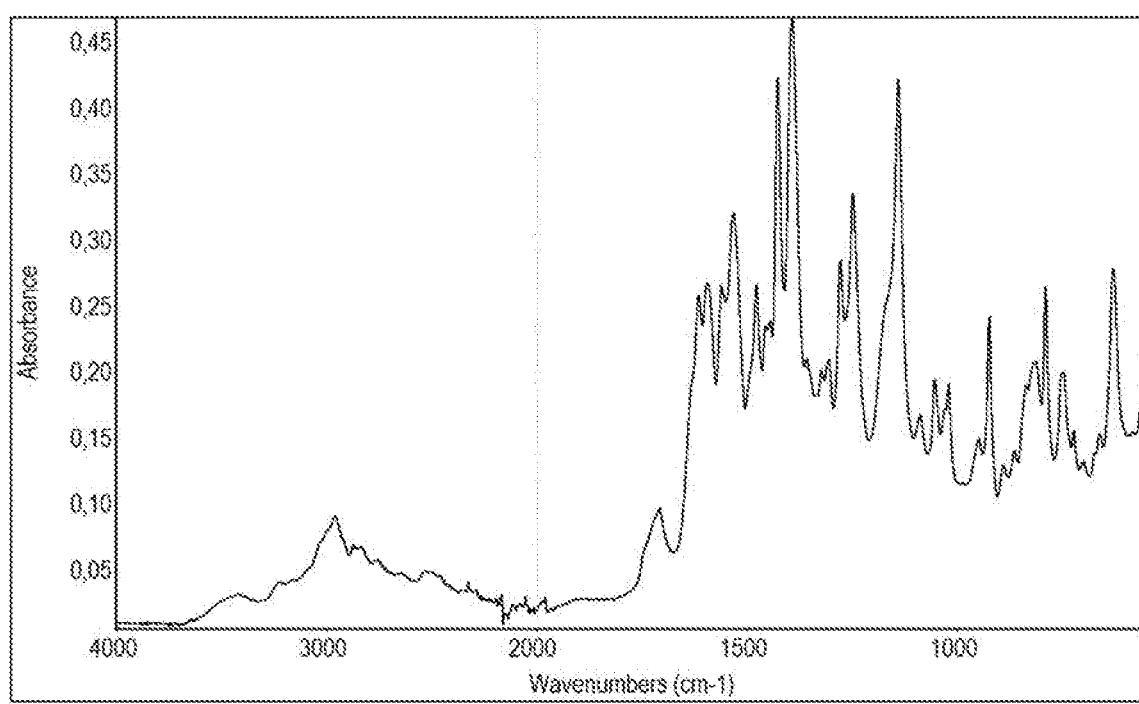

Figure 11: an FTIR spectrum of form C of Ribociclib succinate (1800-550 cm$^{-1}$)
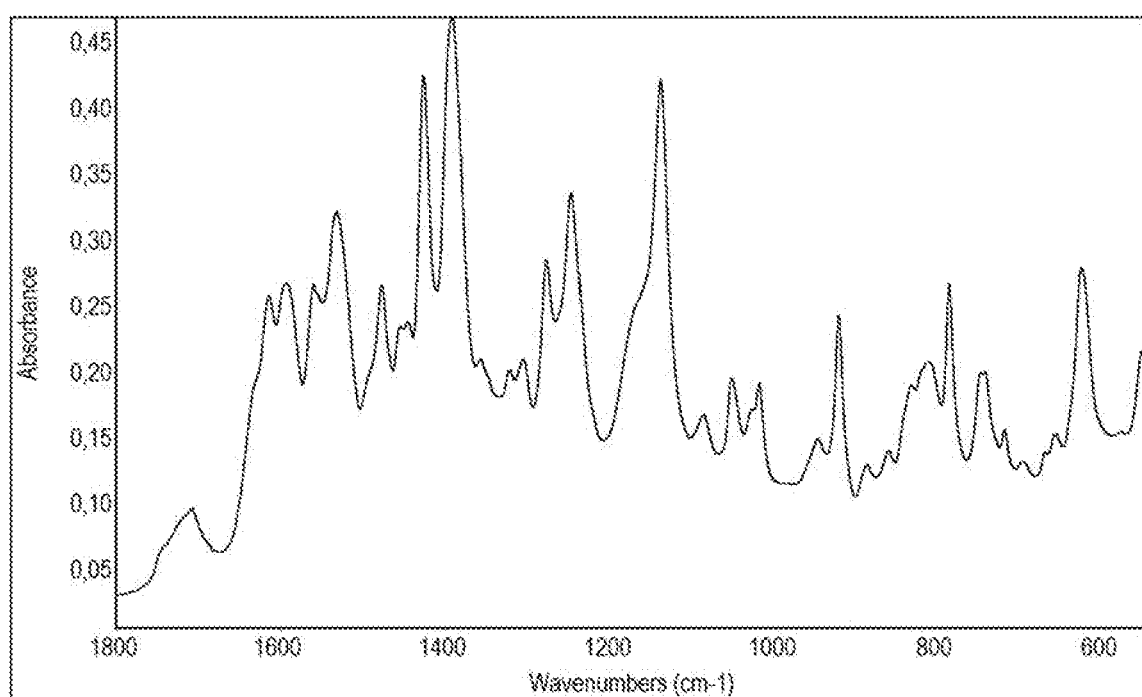

Figure 12: a $^{13}$C Solid state NMR spectrum of form B of Ribociclib succinate (200-0 ppm)
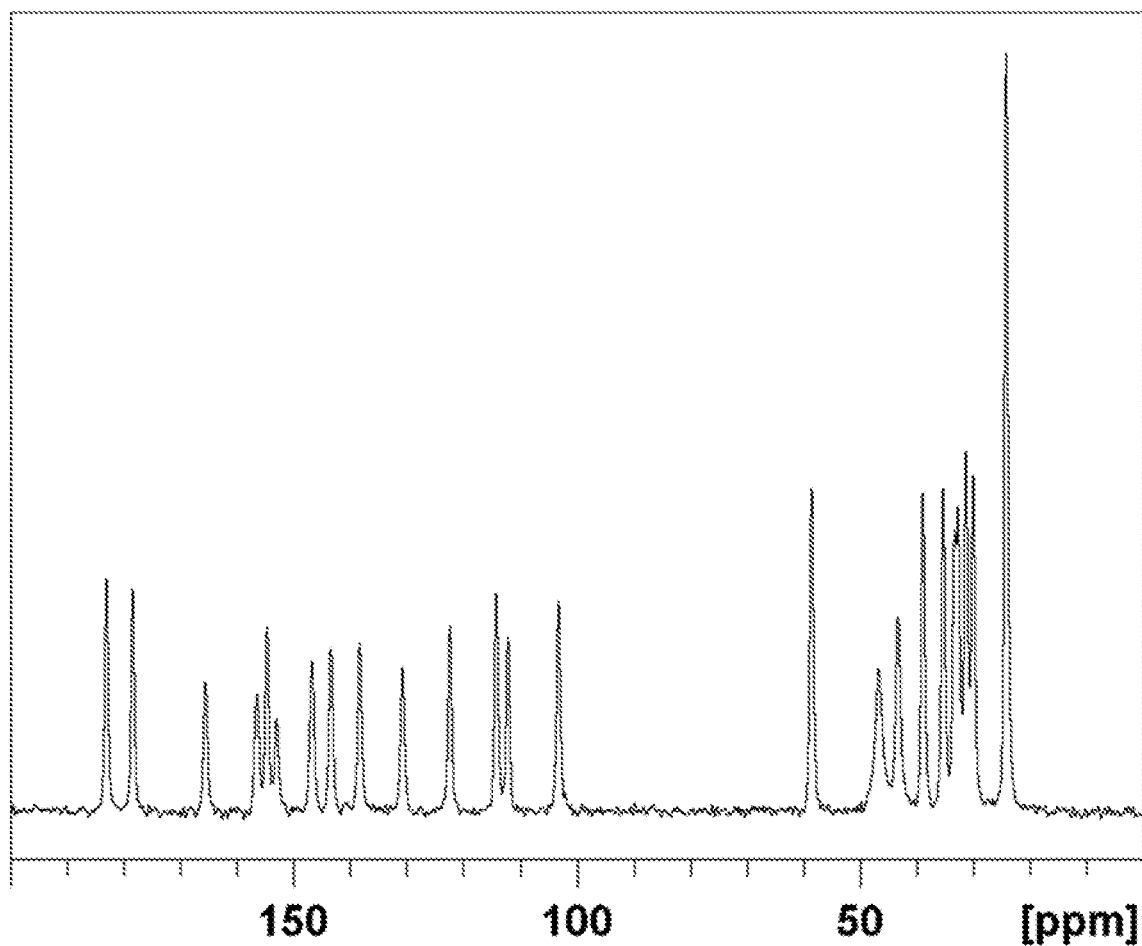

Figure 13: a $^{13}$C Solid state NMR spectrum of form B of Ribociclib succinate (200-100 ppm)
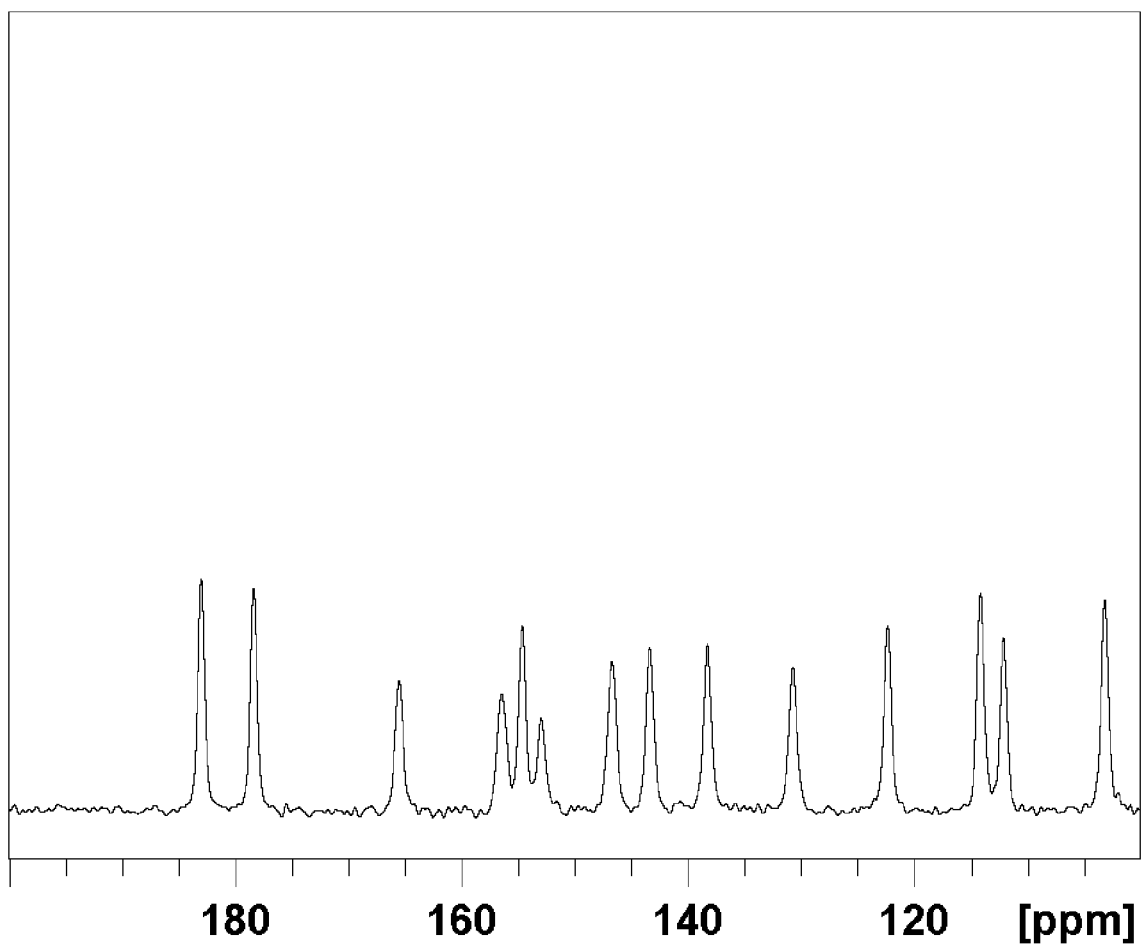

RIBOCICLIB SALTS AND SOLID STATE FORMS THEREOF

CROSS REFERENCE TO RELATED APPLICATIONS

This application is a National Stage Application of, and claims priority to and the benefit of, International Patent Application No. PCT/US2018/047434 filed on Aug. 22, 2018, which, in turn, claims the benefit of, and priority to, U.S. Provisional Application No. 62/550,208 filed Aug. 25, 2017, U.S. Provisional Application No. 62/555,170 filed Sep. 7, 2017, U.S. Provisional Application No. 62/577,446 filed Oct. 26, 2017, and U.S. Provisional Application No. 62/593,319 filed Dec. 1, 2017, the entire disclosures of each of which are incorporated by reference herein.

TECHNICAL FIELD

The present disclosure relates to solid state forms of Ribociclib succinate, processes for preparation thereof, pharmaceutical compositions thereof, and methods of use thereof.

BACKGROUND

Ribociclib, 7-cyclopentyl-N,N-dimethyl-2-{[5-(piperazin-1-yl) pyridin-2-yl]amino}-7H-pyrrolo[2,3-d]pyrimidine-6-carboxamide, has the following formula;

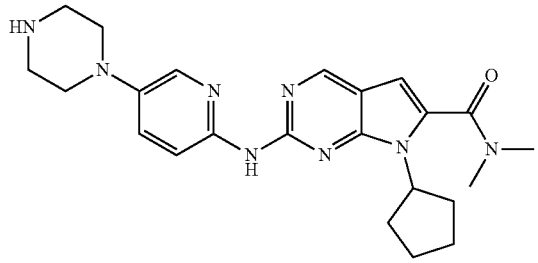 [SMILES: CN(C)C(=O)c1cc2cnc(Nc3ccc(N4CCNCC4)cn3)nc2n1C1CCCC1]

Ribociclib succinate is marketed under the registered trademark KISQALI®. KISQALI® is a kinase inhibitor indicated in combination with an aromatase inhibitor as initial endocrine-based therapy for the treatment of postmenopausal women with hormone receptor (HR)-positive, human epidermal growth factor receptor 2 (HER2)-negative advanced or metastatic breast cancer.

Ribociclib is described in U.S. Pat. No. 8,415,355. Solid state forms of Ribociclib succinate are described in U.S. Pat. No. 9,193,732. EP3156406 discloses crystalline forms of Ribociclib. WO 2016/091221 also discloses crystalline forms of ribociclib succinate, hemisuccinate and several other salts.

Polymorphism, the occurrence of different crystal forms, is a property of some molecules and molecular complexes. A single compound, like Ribociclib succinate, may give rise to a variety of polymorphs having distinct crystal structures and physical properties like melting point (mp), thermal behaviors (e.g. measured by thermogravimetric analysis—"TGA", or differential scanning calorimetry—"DSC"), X-ray powder diffraction (XRPD) pattern, infrared absorption fingerprint, Raman absorption fingerprint, and solid state (13C-) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, improving the dissolution profile, or improving stability (polymorph as well as chemical stability) and shelf-life. These variations in the properties of different salts and solid state forms may also provide improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to use variations in the properties and characteristics of a solid active pharmaceutical ingredient for providing an improved product.

Discovering new solid state forms and solvates of a pharmaceutical product can provide materials having desirable processing properties, such as ease of handling, ease of processing, storage stability, and ease of purification or as desirable intermediate crystal forms that facilitate conversion to other salts or polymorphic forms. New polymorphic forms and solvates of a pharmaceutically useful compound can also provide an opportunity to improve the performance characteristics of a pharmaceutical product (dissolution profile, bioavailability, etc.). It enlarges the repertoire of materials that a formulation scientist has available for formulation optimization, for example by providing a product with different properties, e.g., a different crystal habit, higher crystallinity or polymorphic stability which may offer better processing or handling characteristics, improved dissolution profile, or improved shelf-life. For at least these reasons, there is a need for additional solid state forms (including solvated forms) of Ribociclib succinate.

SUMMARY OF THE DISCLOSURE

The present disclosure relates to solid state forms of Ribociclib succinate, to processes for preparation thereof, and to pharmaceutical compositions thereof.

The present disclosure also relates to other salts of Ribociclib and solid state forms thereof, processes for preparation thereof and to pharmaceutical compositions thereof.

The present disclosure relates to the use of solid state form of Ribociclib succinate, for preparing other solid state forms of Ribociclib succinate, Ribociclib and/or other Ribociclib salts and solid state forms thereof. The present disclosure relates to the use of Ribociclib salts and solid state forms thereof, for preparing Ribociclib and/or other Ribociclib salts and solid state forms thereof.

The present disclosure further provides solid state form of Ribociclib succinate for use in the preparation of other solid state forms of Ribociclib succinate, Ribociclib and/or other Ribociclib salts and solid state forms thereof.

The present disclosure further provides Ribociclib salts and solid state forms thereof for use in the preparation of Ribociclib and/or other Ribociclib salts and solid state forms thereof.

The present disclosure also encompasses the use of the described solid state form of Ribociclib succinate for the preparation of pharmaceutical compositions and/or formulations. The present disclosure also encompasses the use of other Ribociclib salts and solid state form thereof for the preparation of pharmaceutical compositions and/or formulations. The present disclosure further encompasses the described solid state form of Ribociclib succinate for use in the preparation of pharmaceutical compositions and/or formulations for use in medicine, preferably for the treatment of breast cancer.

The present disclosure further encompasses Ribociclib salts and solid state forms thereof for use in the preparation of pharmaceutical compositions and/or formulations for use in medicine, preferably for the treatment of breast cancer.

In another aspect, the present disclosure provides pharmaceutical compositions comprising the solid state forms according to the present disclosure.

In another aspect, the present disclosure provides pharmaceutical compositions comprising other salts of Ribociclib and crystalline forms thereof.

In yet another embodiment, the present disclosure encompasses pharmaceutical formulations comprising the described solid state form of Ribociclib succinate, or of pharmaceutical compositions comprising the solid state form of Ribociclib succinate, and at least one pharmaceutically acceptable excipient.

In yet another embodiment, the present disclosure encompasses pharmaceutical formulations comprising other Ribociclib salts and solid state forms thereof, or of pharmaceutical compositions comprising other Ribociclib salts and solid state forms thereof, and at least one pharmaceutically acceptable excipient.

The present disclosure further encompasses processes to prepare said pharmaceutical formulations of Ribociclib succinate comprising combining the above solid state form of Ribociclib succinate or pharmaceutical compositions comprising it and at least one pharmaceutically acceptable excipient.

The present disclosure further encompasses processes to prepare said pharmaceutical formulations of other Ribociclib salts comprising combining other Ribociclib salts and solid state forms thereof or pharmaceutical compositions comprising them and at least one pharmaceutically acceptable excipient.

The solid state form as defined herein as well as the pharmaceutical compositions or formulations of the solid state form of Ribociclib succinate may be used as medicaments, particularly for the treatment breast cancer.

Other salts of Ribociclib of the present invention as the pharmaceutical compositions or formulations thereof may be used as medicaments, particularly for the treatment breast cancer.

The present disclosure also provides methods of treating breast cancer comprising administering a therapeutically effective amount of the solid state form of Ribociclib succinate of the present disclosure, or at least one of the above pharmaceutical compositions or formulations, to a subject suffering from breast cancer, or otherwise in need of the treatment.

The present disclosure also provides methods of treating breast cancer comprising administering a therapeutically effective amount of another salt of ribociclib or at least one of the above pharmaceutical compositions or formulations, to a subject suffering from breast cancer, or otherwise in need of the treatment.

The present disclosure also provides the uses of the solid state form of Ribociclib succinate of the present disclosure, or at least one of the above pharmaceutical compositions or formulations, for the manufacture of medicaments for treating breast cancer.

The present disclosure also provides the uses of other Ribociclib salts and solid state forms thereof or at least one of the above pharmaceutical compositions or formulations, for the manufacture of medicaments for treating breast cancer.

BRIEF DESCRIPTION OF THE DRAWING

FIG. 1 shows an X-ray powder diffraction (XRPD) pattern of Form II of Ribociclib succinate.
FIG. 2 shows an X-ray powder diffraction (XRPD) pattern of Form B of Ribociclib succinate.
FIG. 3 shows an X-ray powder diffraction (XRPD) pattern of Form C of Ribociclib succinate.
FIG. 4 shows an X-ray powder diffraction (XRPD) pattern obtained by Procedure B of example 3.
FIG. 5 shows an X-ray powder diffraction (XRPD) pattern obtained by Procedure C of example 3.
FIG. 6 shows an X-ray diffraction (XRPD) pattern of Ribociclib succinate obtained by Reference Example 1.
FIG. 7 shows an X-ray powder diffraction (XRPD) pattern of amorphous Ribociclib succinate.
FIG. 8 shows an FTIR spectrum of form B of Ribociclib succinate (full range)
FIG. 9 shows an FTIR spectrum of form B of Ribociclib succinate (1800-550 $cm^{-1}$)
FIG. 10 shows an FTIR spectrum of form C of Ribociclib succinate (full range)
FIG. 11 shows an FTIR spectrum of form C of Ribociclib succinate (1800-550 $cm^{-1}$)
FIG. 12 shows a $^{13}C$ Solid state NMR spectrum of form B of Ribociclib succinate (200-0 ppm)
FIG. 13 shows a $^{13}C$ Solid state NMR spectrum of form B of Ribociclib succinate (200-100 ppm)

DETAILED DESCRIPTION OF THE DISCLOSURE

As discussed earlier, Ribociclib is described in U.S. Pat. No. 8,415,355. Solid state forms of Ribociclib succinate are described in U.S. Pat. No. 9,193,732. EP3156406 discloses crystalline forms of Ribociclib. WO 2016/091221 also discloses crystalline forms of ribociclib hemisuccinate, succinate and several other salts.

The crystalline form disclosed in U.S. Pat. No. 9,193,732 is described as reflecting slight hygroscopic behavior at high humidity conditions that absorbs up to 2% moisture at 90% RH in each cycle. According to the disclosure of U.S. Pat. No. 9,193,732 a steep rise in moisture absorption is observed at 90% RH condition in each cycle and difference in sorption and desorption behavior reflects a formation of hydrate form is taking place at 90% RH condition.

U.S. Pat. No. 9,193,732 also discloses a change in physical form on exposure to 90% RH.

WO 2016/091221 discloses form I of Ribociclib succinate and indicated that form I was stable at high humidity and the solid form didn't change after exposure to 95% RH.

One aspect of the present invention provides a new crystalline form of Ribociclib succinate, designated herein as form B. Form B shows a surprisingly high stability and negligible hygroscopicity. Moreover, the Form B of the present invention is stable to polymorphic changes.

The present disclosure relates to a solid state form of Ribociclib succinate, to processes for the preparation thereof and to pharmaceutical compositions comprising this solid state form and/or combinations thereof. The disclosure also relates to the conversion of Ribociclib succinate of the present disclosure to other solid state forms of Ribociclib succinate. The present disclosure also relates to other salts of Ribociclib and solid state forms thereof, processes for the preparation thereof and to pharmaceutical compositions comprising them.

The disclosure also relates to the conversion of other salts to Ribociclib, Ribociclib succinate and solid state forms thereof.

The solid state forms of Ribociclib succinate or other salts of Ribociclib, according to the present disclosure may have advantageous properties selected from at least one of: chemical or polymorphic purity, flowability, solubility, dissolution rate, bioavailability, morphology or crystal habit, stability—such as chemical stability as well as thermal and mechanical stability with respect to polymorphic conversion, stability towards dehydration and/or storage stability, a lower degree of hygroscopicity, low content of residual solvents, adhesive tendencies and advantageous processing and handling characteristics such as compressibility, and bulk density.

A crystal form may be referred to herein as being characterized by graphical data "as depicted in" a figure. Such data include, for example, powder X-ray diffractograms and solid state NMR spectra. As is well-known in the art, the graphical data potentially provides additional technical information to further define the respective solid state form (a so-called "fingerprint") which can not necessarily be described by reference to numerical values or peak positions alone. In any event, the skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms.

A crystal form of Ribociclib succinate referred to herein as being characterized by graphical data "as depicted in" a Figure will thus be understood to include any crystal forms of the Ribociclib succinate, characterized with the graphical data having such small variations, as are well known to the skilled person, in comparison with the Figure.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% (w/w) or less, about 10% (w/w) or less, about 5% (w/w) or less, about 2% (w/w) or less, about 1% (w/w) or less, or about 0% of any other forms of the subject compound as measured, for example, by XRPD. Thus, solid state of Ribociclib succinate described herein as substantially free of any other solid state forms would be understood to contain greater than about 80% (w/w), greater than about 90% (w/w), greater than about 95% (w/w), greater than about 98% (w/w), greater than about 99% (w/w), or about 100% of the subject solid state form of Ribociclib succinate. Accordingly, in some embodiments of the disclosure, the described solid state form of Ribociclib succinate may contain from about 1% to about 20% (w/w), from about 5% to about 20% (w/w), or from about 5% to about 10% (w/w) of one or more other solid state forms of the same Ribociclib succinate.

As used herein, unless stated otherwise, XRPD peaks reported herein are preferably measured using CuKα radiation, $\lambda=1.5419$ Å. XRPD peaks reported herein are measured using CuK α radiation, $\lambda=1.5419$ Å, at a temperature of 25±3° C.

As used herein, unless stated otherwise, unit cell information was obtained by indexation of synchrotron powder diffraction pattern measured at room temperature.

As used herein, and unless stated otherwise, the term "anhydrous" in relation to crystalline Ribociclib succinate relates to crystalline Ribociclib succinate which does not include any crystalline water (or other solvents) in a defined, stoichiometric amount within the crystal. Moreover, an "anhydrous" form does not contain more than about 1% (w/w) of either water or organic solvents as measured for example by TGA.

The term "solvate," as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

As used herein, the term "isolated" in reference to solid state form of Ribociclib succinate of the present disclosure corresponds to solid state form of Ribociclib succinate that is physically separated from the reaction mixture in which it is formed.

A thing, e.g., a reaction mixture, may be characterized herein as being at, or allowed to come to "room temperature", often abbreviated "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

A process or step may be referred to herein as being carried out "overnight." This refers to a time interval, e.g., for the process or step, that spans the time during the night, when that process or step may not be actively observed. This time interval is from about 8 to about 20 hours, or about 10 to about 18 hours, typically about 16 hours.

The amount of solvent employed in a chemical process, e.g., a reaction or a crystallization may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

As used herein, the term "reduced pressure" refers to a pressure of about 10 mbar to about 500 mbar.

As used herein and unless indicated otherwise, the term "ambient conditions" refer to atmospheric pressure, 22-24° C.

As used herein, the term "non-hydrated form" of Ribociclib succinate refers to the form disclosed in U.S. Pat. No. 9,193,732, which can be prepared according to example 4 therein. Alternatively, non-hydrated form of Ribociclib succinate may be prepared according to reference example 1 or alternatively reference example 2 herein.

The present disclosure comprises a crystalline form of Ribociclib succinate designated Form II. The crystalline Form II of Ribociclib succinate can be characterized by data selected from one or more of the following: an XRPD pattern having peaks at 9.4, 11.5, 17.2 and 18.5 degrees 2-theta±0.2 degrees 2-theta; an XRPD pattern substantially as depicted in FIG. 1; and combinations of these data.

Crystalline Form II of Ribociclib succinate may be further characterized by an XRPD pattern having peaks at 9.4, 11.5, 17.2 and 18.5 degrees two theta±0.2 degrees two theta, and also having one, two, three or four additional peaks selected from 4.6, 13.9, 19.0 and 23.2 degrees two theta±0.2 degrees two theta.

In one embodiment of the present disclosure, crystalline form II of Ribociclib succinate is isolated.

Crystalline Form II of Ribociclib succinate may be anhydrous.

Crystalline Form II of Ribociclib succinate may be polymorphically pure.

Crystalline form of the invention may be characterized by a mp of 189-190° C.

In another aspect, the present disclosure comprises a crystalline form of Ribociclib succinate designated Form B. The crystalline Form B of Ribociclib succinate can be characterized by data selected from one or more of the following: an XRPD pattern having peaks at 6.5, 7.5, 10.2, 10.9 and 12.0 degrees two theta±0.2 degrees two theta; an XRPD pattern substantially as depicted in FIG. 2; a solid state $^{13}$C NMR spectrum substantially as depicted in FIG. 12 or in FIG. 13; a solid state $^{13}$C NMR spectrum having peaks at 183.0, 165.5, 156.5, 138.3 and 103.1 ppm±0.2 ppm; a solid state $^{13}$C NMR spectrum having the following chemical shift absolute differences between said characteristic peaks at 183.0, 165.5, 156.5, 138.3 and 103.1 ppm±0.2 and a reference peak at 122.3 ppm±1 ppm of 60.7, 43.2, 34.1, 15.9 and (−19.2)±0.1 ppm; an FT-IR spectrum substantially as depicted in FIG. 8 or in FIG. 9; an FT-IR spectrum having absorptions at 1605, 1525, 1399, 1261 and 786 cm$^{-1}$±4 cm$^{-1}$; and combinations of these data.

Alternatively, form B of ribociclib succinate can be characterized by the following unit cell data:

| | |
|---|---|
| cell_length_a | 13.88 Å |
| cell_length_b | 12.79 Å |
| cell_length_c | 8.89 Å |
| cell_angle_alpha | 67.93° |
| cell_angle_beta | 98.16° |
| cell_angle_gamma | 96.12° |
| cell_volume | 1445 Å$^3$ |
| cell_measurement_temperature, | 293 K |
| symmetry_cell_setting | triclinic |
| symmetry_space_group_name_H-M | P -1 |

Form B of ribociclib succinate can be characterized by any combination of the above data.

Crystalline Form B of Ribociclib succinate may be further characterized by an XRPD pattern having peaks at 6.5, 7.5, 10.2, 10.9 and 12.0 degrees two theta±0.2 degrees two theta, and also having one, two, three, four or five additional peaks selected from 14.6, 20.2, 20.7, 25.4 and 26.6 degrees two theta±0.2 degrees two theta.

Crystalline form B of Ribociclib succinate may be further characterized by the data set forth in the following table.

TABLE 2

X-ray powder diffraction peaks of form B of Ribociclib succinate. peak position (degrees two theta ± 0.2 degrees two theta)

| |
|---|
| 6.5 |
| 7.5 |
| 9.6 |
| 10.2 |
| 10.9 |
| 12.0 |
| 14.6 |
| 16.0 |
| 18.0 |
| 19.2 |
| 20.2 |
| 20.7 |
| 21.1 |
| 21.5 |
| 22.8 |
| 23.3 |
| 25.4 |
| 26.0 |
| 26.6 |
| 28.2 |
| 29.3 |
| 30.2 |
| 30.6 |
| 31.6 |
| 34.0 |
| 39.0 |

In some embodiments, Crystalline form B of Ribociclib succinate may be a hydrate. In certain embodiments form B may contain from about 2% to about 7% of water by weight, preferably about 6% of water by weight as measured by Karl Fischer titration and/or Thermal gravimetric analysis (TGA) and/or by crystal structure analysis from synchrotron powder XRD data. In certain embodiments, crystalline form B of Ribociclib succinate may be a dihydrate.

In one embodiment of the present disclosure, crystalline form B of Ribociclib succinate is isolated.

In another aspect, the present disclosure comprises a crystalline form of Ribociclib succinate designated Form C. The crystalline Form C of Ribociclib succinate can be characterized by data selected from one or more of the following: an XRPD pattern having peaks at 8.4, 12.0, 18.4 and 20.5 degrees two theta±0.2 degrees two theta; an XRPD pattern substantially as depicted in FIG. 3; an FT-IR spectrum substantially as depicted in FIG. 10 or in FIG. 11; an FT-IR spectrum having absorptions at 1427, 1392, 1248, 1139 and 628 cm$^{-1}$±4 cm$^{-1}$; and combinations of these data.

Crystalline Form C of Ribociclib succinate may be further characterized by an XRPD pattern having peaks at 8.4, 12.0, 18.4 and 20.5 degrees two theta±0.2 degrees two theta, and also having one, two, three or four additional peaks selected from 11.0, 17.8, 19.5 and 21.9 degrees two theta±0.2 degrees two theta.

In one embodiment of the present disclosure, crystalline form C of Ribociclib succinate is isolated. In another embodiment crystalline form C of Ribociclib succinate is polymorphically pure.

The present disclosure also relates to processes for preparation of crystalline form B of Ribociclib succinate.

In another embodiment, the disclosure relates to a process for preparation of crystalline form B ribociclib succinate which process comprises a) providing ribociclib succinate in a solvent system comprising water and ethanol; b) optionally heating; c) optionally cooling; d) optionally seeding with form B seeds and e) isolating crystalline form B.

Preferably the process of the present disclosure is performed with stirring.

Preferably ribociclib succinate in step a) is non-hydrated ribociclib succinate.

Preferably the solvent system in step a) consists of water and ethanol

Preferably the mixture of water and ethanol in step a) comprises about equal parts of water and ethanol.

Preferably in step a) a slurry is formed.

In a particularly preferred embodiment, the disclosure provides a process for preparing crystalline form B ribociclib succinate comprising slurrying ribociclib succinate (preferably non-hydrate form) in a mixture of water and ethanol, preferably with stirring. More preferably, the process is carried out at room temperature for a sufficient time to convert the starting material to form B ribociclib succinate (preferably for 6-48 hours, 10-36 hours, or 18-24 hours).

The crystalline form B can be separated by any method known in the art, for example by filtering the slurry or decanting the solvent from the slurry. The isolation can further comprise washing and/or drying the product.

In any of the above processes, the Ribociclib succinate can be further combined with a pharmaceutically acceptable excipient to prepare a pharmaceutical composition.

In another aspect the present disclosure relates to form B produced by the processes of the invention.

The present disclosure also relates to other salts of ribociclib and solid state forms thereof, processes for preparation thereof and to pharmaceutical compositions thereof.

The present disclosure also relates to the use of the solid state form of Ribociclib succinate of the present disclosure, for preparing other solid state forms of Ribociclib succinate, Ribociclib and/or other Ribociclib salts and solid state forms thereof.

The present disclosure relates to the use of Ribociclib salts and solid state forms thereof, for preparing Ribociclib and/or other Ribociclib salts and solid state forms thereof, The present disclosure further provides solid state form of Ribociclib succinate for use in the preparation of other solid state form of Ribociclib succinate, Ribociclib and/or other Ribociclib salts and solid state forms thereof.

The present disclosure further provides Ribociclib salts and solid state forms thereof for use in the preparation of Ribociclib and/or other Ribociclib salts and solid state forms thereof.

The present disclosure also encompasses the use of the described solid state form of Ribociclib succinate for the preparation of pharmaceutical compositions and/or formulations.

The present disclosure also encompasses the use of other Ribociclib salts and solid state form thereof for the preparation of pharmaceutical compositions and/or formulations.

The present disclosure further encompasses the described solid state form of Ribociclib succinate for use in the preparation of pharmaceutical compositions and/or formulations for use in medicine, preferably for the treatment of breast cancer.

The present disclosure further encompasses Ribociclib salts and solid state forms thereof for use in the preparation of pharmaceutical compositions and/or formulations for use in medicine, preferably for the treatment of breast cancer.

In another aspect, the present disclosure provides pharmaceutical compositions comprising the solid state form according to the present disclosure.

In another aspect, the present disclosure provides pharmaceutical compositions comprising other salts of ribociclib and crystalline forms thereof.

In yet another embodiment, the present disclosure encompasses pharmaceutical formulations comprising the described solid state form of Ribociclib succinate, or of pharmaceutical compositions comprising the solid state form of Ribociclib succinate, and at least one pharmaceutically acceptable excipient.

In yet another embodiment, the present disclosure encompasses pharmaceutical formulations comprising other Ribociclib salts and solid state forms thereof, or of pharmaceutical compositions comprising other Ribociclib salts and solid state forms thereof, and at least one pharmaceutically acceptable excipient.

The present disclosure further encompasses processes for preparing Ribociclib salts or solid state forms thereof. The process comprises preparing the solid state form of the present disclosure, and converting it to other solid state form of Ribociclib. Alternatively, the process comprises preparing the solid state form of the present disclosure, and converting it to Ribociclib salt. The conversion can be done, for example, by a process comprising reacting the obtained Ribociclib with an appropriate acid to obtain the corresponding salt.

The present disclosure further encompasses processes to prepare said pharmaceutical formulations of Ribociclib succinate comprising combining Ribociclib succinate of the present disclosure, or pharmaceutical compositions comprising it, and at least one pharmaceutically acceptable excipient.

The present disclosure further encompasses processes to prepare said pharmaceutical formulations of other Ribociclib salts comprising combining other Ribociclib salts and solid state forms thereof or pharmaceutical compositions comprising them and at least one pharmaceutically acceptable excipient. The solid state form as defined herein as well as the pharmaceutical compositions or formulations of the solid state form of Ribociclib succinate may be used as medicaments, particularly for the treatment of breast cancer.

Other salts of Ribociclib of the present invention as the pharmaceutical compositions or formulations thereof may be used as medicaments, particularly for the treatment breast cancer.

The present disclosure also provides methods of treating breast cancer comprising administering a therapeutically effective amount of the solid state form of Ribociclib succinate of the present disclosure, or at least one of the above pharmaceutical compositions or formulations, to a subject suffering breast cancer, or otherwise in need of the treatment.

The present disclosure also provides methods of treating breast cancer comprising administering a therapeutically effective amount of another salt of ribociclib or at least one of the above pharmaceutical compositions or formulations, to a subject suffering from breast cancer, or otherwise in need of the treatment.

The present disclosure also provides the uses of the solid state form of Ribociclib succinate of the present disclosure, or at least one of the above pharmaceutical compositions or formulations, for the manufacture of medicaments for treating breast cancer. The present disclosure also provides the uses of other Ribociclib salts and solid state forms thereof or at least one of the above pharmaceutical compositions or formulations, for the manufacture of medicaments for treating breast cancer.

In yet another aspect, the present disclosure provides other salts of Ribociclib, selected from the group consisting of: Ribociclib hydrochloride, Ribociclib mesylate, Ribociclib acetate, Ribociclib oxalate, Ribociclib tosylate, Ribociclib sulfate, Ribociclib phosphate and Ribociclib malate or a solid state form thereof, as well as processes for preparation thereof and to pharmaceutical compositions thereof.

The Ribociclib hydrochloride, Ribociclib mesylate, Ribociclib acetate, Ribociclib oxalate, Ribociclib tosylate, Ribociclib sulfate, Ribociclib phosphate and Ribociclib malate may be in crystalline form or may be in an amorphous form. Preferably, the Ribociclib salt is in crystalline form.

The present disclosure also relates to the use of a Ribociclib salt selected from the group consisting of: Ribociclib hydrochloride, Ribociclib mesylate, Ribociclib acetate, Ribociclib oxalate, Ribociclib tosylate, Ribociclib sulfate, Ribociclib phosphate and Ribociclib malate for preparing Ribociclib and Ribociclib succinate, and/or other Ribociclib salts and solid state forms thereof.

The present disclosure further provides a Ribociclib salt selected from the group consisting of: Ribociclib hydrochloride, Ribociclib mesylate, Ribociclib acetate, Ribociclib oxalate, Ribociclib tosylate, Ribociclib sulfate, Ribociclib phosphate and Ribociclib malate for use in the preparation of Ribociclib succinate, Ribociclib and/or other Ribociclib salts and solid state forms thereof.

The present disclosure also encompasses the use of a Ribociclib salt selected from the group consisting of: Ribociclib hydrochloride, Ribociclib mesylate, Ribociclib acetate, Ribociclib oxalate, Ribociclib tosylate, Ribociclib sulfate, Ribociclib phosphate, and Ribociclib malate, and a solid state form thereof, for the preparation of pharmaceutical compositions and/or formulations.

The present disclosure also encompasses the use of a Ribociclib salt selected from the group consisting of: Ribociclib hydrochloride, Ribociclib mesylate, Ribociclib acetate, Ribociclib oxalate, Ribociclib tosylate, Ribociclib sulfate, Ribociclib phosphate and Ribociclib malate, and solid state form thereof for the preparation of pharmaceutical compositions and/or formulations.

The present disclosure further encompasses a Ribociclib salt selected from the group consisting of: Ribociclib hydrochloride, Ribociclib mesylate, Ribociclib acetate, Ribociclib oxalate, Ribociclib tosylate, Ribociclib sulfate, Ribociclib phosphate and Ribociclib malate for use in the preparation of pharmaceutical compositions and/or formulations for use in medicine, preferably for the treatment of breast cancer.

The present disclosure further encompasses a Ribociclib salt selected from the group consisting of: Ribociclib hydrochloride, Ribociclib mesylate, Ribociclib acetate, Ribociclib oxalate, Ribociclib tosylate, Ribociclib sulfate, Ribociclib phosphate and Ribociclib malate, for use in the preparation of pharmaceutical compositions and/or formulations for use in medicine, preferably for the treatment of breast cancer.

In another aspect, the present disclosure provides pharmaceutical compositions comprising a Ribociclib salt selected from the group consisting of: Ribociclib hydrochloride, Ribociclib mesylate, Ribociclib acetate, Ribociclib oxalate, Ribociclib tosylate, Ribociclib sulfate, Ribociclib phosphate and Ribociclib malate.

In yet another embodiment, the present disclosure encompasses pharmaceutical formulations comprising a Ribociclib salt selected from the group consisting of: Ribociclib hydrochloride, Ribociclib mesylate, Ribociclib acetate, Ribociclib oxalate, Ribociclib tosylate, Ribociclib sulfate, Ribociclib phosphate and Ribociclib malate, and at least one pharmaceutically acceptable excipient.

The present disclosure further encompasses processes for preparing a Ribociclib salt selected from the group consisting of: Ribociclib hydrochloride, Ribociclib mesylate, Ribociclib acetate, Ribociclib oxalate, Ribociclib tosylate, Ribociclib sulfate, Ribociclib phosphate, and Ribociclib malate. The process comprises combining Ribociclib base, with the corresponding acid, in a solvent, and isolating the Ribociclib salt from the mixture.

Pharmaceutical formulations of the present invention contain any one or a combination of the solid state forms of Ribociclib succinate, or any one or a combination of Ribociclib salts selected from the group consisting of: Ribociclib hydrochloride, Ribociclib mesylate, Ribociclib acetate, Ribociclib oxalate, Ribociclib tosylate, Ribociclib sulfate, Ribociclib phosphate, and Ribociclib malate according to the present invention, particularly crystalline form B of ribociclib succinate. Particularly, in addition to Ribociclib succinate (or other salt of Ribociclib according to the invention), the pharmaceutical formulations of the present invention can contain other active ingredients, such as for example Letrozole, and one or more excipients. Excipients are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present invention include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, ibandronate sodium and any other solid excipients are dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present invention, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present invention include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, the most preferred route of the present invention is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present invention can be a capsule containing the composition, preferably a powdered or granulated solid composition of the invention, within either a hard or soft shell. The shell can be made from gelatin and optionally contain a plasticizer such as glycerin and sorbitol, and an opacifying agent or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present invention can comprise any of the aforementioned blends and granulates that were described with reference to tableting, but they are not subjected to a final tableting step.

A pharmaceutical formulation of Ribociclib succinate can be administered. Ribociclib succinate is preferably formulated for administration to a mammal, preferably a human, by injection. Ribociclib succinate can be formulated, for example, as a viscous liquid solution or suspension, preferably a clear solution, for injection. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al., Pharmaceutical Dosage Forms and Drug Delivery Systems, 7th ed.

Having described the disclosure with reference to certain preferred embodiments, other embodiments will become apparent to one skilled in the art from consideration of the specification. The disclosure is further illustrated by reference to the following example describing in detail the preparation of the composition and methods of use of the disclosure. It will be apparent to those skilled in the art that many modifications, both to materials and methods, may be practiced without departing from the scope of the disclosure.

Analytical Methods
X-Ray Powder Diffraction Method Used for FIG. 1 (Example 1), FIG. 3 (Example 3, Procedure A), FIG. 4 (Example 3, Procedure B), FIG. 5 (Example 3, Procedure C), FIG. 6 (Reference Example 1) and FIG. 7 (Example 4):

Sample after being powdered in a mortar and pestle is applied directly on a silicon plate holder. The X-ray powder diffraction pattern was measured with Philips X'Pert PRO X-ray powder diffractometer, equipped with Cu irradiation source=1.54184 Å (Ångstrom), X'Celerator (2.022° 2θ) detector. Scanning parameters: angle range: 3-40 deg., step size 0.0167, time per step 37 s, continuous scan.

X-Ray Powder Diffraction Method Used for FIG. 2 (Example 2):

Powder X-ray Diffraction was performed on PANalytical X'Pert Pro X-Ray powder diffractometer; CuKα radiation (λ=1.54187 Å); X'Celerator detector with active length 2.1221 degrees two theta; laboratory temperature 25±2° C.; zero background sample holders. Prior to analysis, the samples were gently ground using a mortar and pestle to obtain a fine powder.

Measurement Parameters:

| | |
|---|---|
| Scan range | 3-40 degrees two theta |
| Scan mode | continuous |
| Step size | 0.0167 degrees |
| Time per step | 42 s |
| Sample spin | 60 rpm |

$^{13}$C CP/MAS NMR Method:

The $^{13}$C CP/MAS NMR spectrum was measured at 125 MHz using Bruker Avance 500 WB/US NMR spectrometer (Karlsruhe, Germany, 2003) at magic angle spinning (MAS) frequency $\omega_r/2=20$ kHz. In all cases finely powdered samples were placed into the 4 mm ZrO2 rotors and standard CPMAS pulseprogram was used. During acquisition of the data a high-power dipolar decoupling TPPM (two-pulse phase-modulated) was applied. The number of scans was 1024, repetition delay was 10 s. Taking into account frictional heating of the samples during fast rotation all NMR experiments were performed at 298 K (precise temperature calibration was performed).

The $^{13}$C scale was calibrated with glycine as external standard (176.03 ppm—low-field carbonyl signal). The NMR spectrometer was completely calibrated and all experimental parameters were carefully optimized prior the investigation. Magic angle was set using KBr during standard optimization procedure and homogeneity of magnetic field was optimized using adamantane sample (resulting line-width at half-height $\Delta v_{1/2}$ was less than 3.5 Hz at 250 ms of acquisition time).

Fourier transform infrared spectroscopy ("FTIR") method:
FTIR spectrum was recorded on:
Equipment: Nicolet 380 FTIR Spectrometer
Mode: ATR (diamond);
Spectral range: 4000-550 cm−1;
Sample/bckg gain: 8.0;
Number of scans: 128;
Resolution: 4.0 cm−1

EXAMPLES

The starting material, Ribociclib free base can be prepared according to example 3 of U.S. Pat. No. 9,193,732.

Non-hydrated Ribociclib succinate can be prepared according to example 4 of U.S. Pat. No. 9,193,732 or alternatively according to the reference examples 1 or 2.

Reference Example 1

In a 0.5 L reactor under inert conditions (nitrogen) succinic acid (11.2 g, 1.05 eq) was suspended in i-PrOH (314.4 mL, 8.0 v/w). The suspension was heated to 60±3° C. and a clear solution was obtained. The solution was then filtered on a P3 gooch and kept under stirring at 25±3° C.

In a 2 L reactor under inert conditions (nitrogen) Ribociclib (39.3 g, 1.0 eq) was suspended in i-PrOH (1414.8 mL, 36.0 v/w) and heated to 80±3° C. until dissolution. The solution was cooled down to 70±3° C. and filtered on a dicalite pad. The filtered solution was transferred in 2 L reactor and heated to 80±3° C. The succinic acid solution in i-PrOH was added dropwise in 0.5 h maintaining T=80±3° C. The mixture was kept under stirring at 80±3° C. for 0.5 h and then it was cooled down to 20±3° C. in 3.5 h. Upon 0.5 h stirring at this temperature, the solid was filtered off and washed with i-PrOH (20 mL, 1 v/w). The solid was dried in oven under vacuum at 50° C. until constant weight. Ribociclib succinate was obtained as a yellow solid (38.3 g, 76.6% yield, 99.8% purity). The obtained solid was analyzed by XRPD and the XRPD pattern is presented in FIG. 6.

The ratio of Ribociclib succinate to isopropanol (about 3:1) (~3.4% isopropanol) was determined by 1H NMR: 1H NMR (ppm; DMSO-d6): 3.78 (m, 1H) (isopropanol-CH), 4.75 (m, 1H) (Ribociclib pyrrole-CH).

Reference Example 2

In a reactor, succinic acid (1.45 g, 1.05 eq.) was dissolved in 2-propanol (40 mL) at 65° C. obtaining a clear solution. The solution at 65° C. is filtered on a 0.45 µm membrane and the filtrate is kept at 30° C. In the meanwhile Ribociclib free base (5 g, 1.0 eq.) was dissolved in 2-propanol (185 mL) at 80° C. and the obtained yellow solution was filtrated through a pad of dicalite (3.2 g). The solution of succinic acid was added to the ribociclib free base solution at 80° C. within 45 minutes and precipitation was observed after 35 minutes. At the end of the loading the solution was stirred for 1 hour at 80° C. Afterwards the mixture was cooled to 20° C. in 1 hour and stirred for 30 minutes at 20° C. The obtained suspension was filtrated, washed with 2-propanol (25 mL) and dried in oven at 60° C. for 16 hours to obtain 5.4 g of RBC succinate.

Example 1: Preparation Of Form II of Ribociclib Succinate

In a reactor under inert conditions (nitrogen), succinic acid (2.9 g) and 2-propanol (80 mL) were stirred and warmed to 65° C. to obtain a clear solution. The solution was filtered hot and kept at 30° C. (solution A). Ribociclib free base (10 g) and 2-propanol (370 mL) were stirred and heated to 80° C. to obtain a solution. The solution was cooled to 70° C. and filtered through a pad of dicalite. The Ribociclib base solution was heated to 80° C. and solution A was added within one hour. Upon completion of the addition, the mixture was stirred for 1 h at 80° C., then cooled to room temperature and stirred for 30 minutes. The obtained solid was filtered, washed with 2-propanol (50 mL) and part of the material was dried at 60° C./10 mbar for 18 h to afford 5.3 g of Ribociclib succinate with mp 189-190° C. The solid was analyzed by XRPD and the XRPD pattern is presented in FIG. 1.

Example 2: Preparation of Form B of Ribociclib Succinate 0.1 g of Ribociclib succinate form II, prepared according to example 1, was put into a hygroscopicity chamber and it was exposed to 100% RH at room temperature for 3 days. The product was analyzed by XRPD and the XRPD pattern is presented in FIG. 2.

Example 3: Preparation of Form C of Ribociclib Succinate

Procedure A

In a glove box under inert atmosphere (nitrogen), succinic acid (5.8 g) was suspended in water (8 mL) at 90° C., affording a clear solution. The solution was then cooled down to 70° C. and precipitation of solid material occurred. Ribociclib base (2.5 g) was added and the mixture was heated until complete solution was achieved at 70° C. (solution A). In a 100 mL reactor, seed of Ribociclib succinate form II (0.2 g, prepared according to example 1) was suspended in acetone (50 mL, solution B) at 10° C. Then, hot solution A was added dropwise to solution B. During addition a suspension was always present in the receiving reactor. The suspension was filtered after 15 min and the solid was dried under vacuum at 60° C. for 16 h (2.1 g, 66.0% yield, 99.47% purity). The product was analyzed by XRPD and the XRPD pattern is presented in FIG. 3.

Procedure B

In a glove box under inert atmosphere (nitrogen), a solution of succinic acid (0.8 g) in water (9.6 mL) was prepared at 50° C. (solution A). Ribociclib base (2.8 g) was charged in a 100 mL reactor. Solution A was added to Ribociclib base. The mixture was further diluted with water (10 mL), then succinic acid (0.72 g) was added to the mixture affording complete dissolution. Water was then distilled under vacuum to a residual volume of 10 mL at 50° C. Acetone (56 mL) was added at 50° C. and precipitation was observed after addition of about 30 mL of acetone. The suspension was then cooled down to 0° C. in 1 h and kept under stirring at 0° C. for 30 min. The solid was isolated by filtration and washed with acetone (10 mL). Ribociclib succinate was dried under vacuum at 50° C. for 18 h (2.8 g, 78.7% yield, 99.04% purity). The product was analyzed by XRPD and the XRPD pattern is presented in FIG. 4.

Procedure C

Non-hydrated Ribociclib succinate (500 mg) was milled in a ball mill for 3 hours at 800 rpm (agate jar with 5 agate balls). Obtained solid (100 mg) was stirred in a slurry of dichloromethane (1 mL) at room temperature for 2 days. Solid was filtered and analyzed by XRPD and the XRPD pattern is presented in FIG. 5.

Procedure D

In a glove box under inert atmosphere (nitrogen), a solution of succinic acid (4.35 g) in water (8 mL) was prepared at 80° C. Ribociclib base (2 g) was added. Complete solution at 80° C. was achieved (solution A). In a 100 mL reactor acetone (50 mL) was charged at 10° C. Solution A was added dropwise in 5 minutes to acetone. Upon 5 minutes stirring at 10° C., precipitation occurred. The suspension was then kept under stirring at 10° C. and split into two aliquots. First aliquot of the suspension was filtered after 1 h stirring at 10° C. and solid was dried under vacuum at 60° C. for 16 h (0.65 g, 99.34% purity). Second aliquot was kept for two days at 10° C. under stirring and then filtered. The solid was dried under vacuum at 60° C. for 16 h (1.25 g, 99.50% purity). The product of each aliquot was analyzed by XRPD and both were identified as form C of Ribociclib Succinate.

Procedure E

In a glove box under inert atmosphere (nitrogen), a solution of Ribociclib base (3 g) and succinic acid (6.52 g) was prepared in a mixture of water (12 mL) and acetone (75 mL) at 50° C. The resulting solution was filtered on a dicalite pad, then cooled down to 20° C. spontaneously and kept under stirring at this temperature for 16 h. After 16 h the solution was cooled down to 10° C. in 0.5 h and seed (150 mg of form C, prepared according to procedure D of example 3, 2nd aliquot, 5 w./w. %) was added. Precipitation occurred and the suspension was kept under stirring at this temperature for 6 h. The solid was isolated by filtration, washed with acetone (15 mL×2 times) and dried under vacuum in oven at 60° C. for 70 h (2.7 g, 99.56% purity, 68% yield). The product was analyzed by XRPD and identified as form C of Ribociclib Succinate.

Example 4: Preparation of Amorphous Ribociclib Succinate

Ribociclib succinate (900 mg) was dissolved in water (10 mL) at room temperature. The obtained solution was freeze-dried at −40° C. The obtained solid was analyzed by XRPD and the XRPD pattern is presented in FIG. 7.

Example 5: Preparation of Ribociclib

Under inert atmosphere, tert-butyl 4-(6-(6-(dimethylcarbamoyl)-7-cyclopentyl-7H-pyrrolo[2,3-d]pyrimidin-2-ylamino)pyridin-3-yl)piperazine-1-carboxylate (40.0 g) was suspended in 3:1 water/acetone mixture (800 mL) and the suspension was heated to 50° C. Aq. hydrochloric acid 6 M (60.8 mL) was added dropwise in 10 min and the mixture was kept under stirring at 50° C. for 2 h. At the end of reaction, the solution was cooled down to 25° C. and filtrated on a dicalite pad. Aq. 10% sodium hydroxide (136 mL) was added dropwise in 10 min and the suspension was kept under stirring for 30 min. Ribociclib base was isolated by filtration, washed with water (120 mL) and dried under vacuum at 20° C. for 16 h. Ribociclib was obtained as a solid (66.1% yield).

Example 6: Preparation of Ribociclib HCl

Under inert atmosphere, Ribociclib base (4.0 g) was suspended in water (12 mL), then aq. hydrochloric acid 37% (1.8 mL) was added at 20° C. The suspension was kept under stirring for 20 min achieving complete dissolution. Acetone (80 mL) was added dropwise in 20 min to the Ribociclib solution. The mixture was cooled down to 0° C. in 1 h, then kept under stirring at 0° C. for 2 h. Ribociclib hydrochloride was isolated by filtration, washed with acetone (12 mL) and dried under vacuum at 50° C. for 16 h. Ribociclib hydrochloride was obtained as a yellow solid (95.5% yield).

Example 7: Preparation of Ribociclib Mesylate

Under inert atmosphere, Ribociclib base (4.0 g) was suspended in water (12 mL), then methane sulfonic acid (1.2 mL) was added at 20° C. The suspension was kept under stirring for 20 min achieving complete dissolution. Acetone (60 mL) was added dropwise in 15 min to the ribociclib solution. The mixture was cooled down to −5° C. in 1 h. No solid formation was observed. Additional acetone (100 mL) was added, causing product precipitation. The suspension was kept under stirring at −5° C. for 2 h. Ribociclib mesylate was isolated by filtration, washed with acetone (12 mL) and dried under vacuum at 50° C. for 16 h. Ribociclib mesylate was obtained as a solid (91.2% yield).

Example 8: Preparation of Ribociclib Acetate

Under inert atmosphere, Ribociclib base (4.0 g) was suspended in water (12 mL), then acetic acid (1.1 mL) was added at 20° C. The suspension was kept under stirring for 30 min achieving complete dissolution. Acetone (80 mL) was added dropwise in 10 min to the ribociclib solution. The mixture was cooled down to 0° C. in 1 h, then kept under stirring at 0° C. for 1.5 h. Ribociclib acetate was isolated by filtration, washed with acetone (12 mL) and dried under vacuum at 50° C. for 16 h. Ribociclib acetate was obtained as a white solid (93.2% yield).

Example 9: Preparation of Ribociclib Oxalate

Under inert atmosphere, Ribociclib base (5.0 g) was suspended in i-PrOH (125 mL), then oxalic acid (5.5 g) was added at 20° C. The suspension was heated to 60° C. and a cloudy solution was obtained. The mixture was filtrated on a dicalite pad. The solution was cooled down to 0° C. in 1 h, then kept under stirring at 0° C. for 1.5 h. Ribociclib oxalate was isolated by filtration, washed with i-PrOH (10 mL) and dried under vacuum at 20° C. for 2 days and at 50° C. for 6 h. Ribociclib oxalate was obtained as a solid (4.8 g, 79.5% yield).

Example 10: Preparation of Ribociclib Tosylate

Under inert atmosphere, a solution of p-toluene sulfonic acid monohydrate (2.7 g) in water (9 mL) was added to ribociclib base (3.0 g) at 20° C. The suspension was kept under stirring for 1 h at 20° C. achieving complete dissolution. Acetone (60 mL) was added dropwise in 10 min to the Ribociclib solution. The mixture was cooled down to 0° C. in 1 h, no solid formation was observed. Upon addition of acetone (60 mL), a suspension was obtained, which was then kept under stirring at 0° C. for 1.5 h. Ribociclib tosylate was isolated by filtration, washed with acetone (6 mL) and dried under vacuum for 18 h. Ribociclib Tosylate was obtained as a solid (4.3 g, 100% yield).

Example 11: Preparation of Ribociclib Sulfate

Under inert atmosphere, a solution of sulfuric acid (1.4 g) in water (9 mL) was added at 20° C. to ribociclib base (3.0 g). The suspension was kept under stirring for 1.5 h at 20° C. achieving complete dissolution. Acetone (60 mL) was added dropwise in 10 min to the Ribociclib solution. The resulting suspension was kept under stirring at 20° C. for 1.5 h. Ribociclib sulfate was isolated by filtration, washed with acetone (6 mL) and dried under vacuum at 50° C. for 18 h. Ribociclib sulfate was obtained as a solid (3.8 g, 100% yield).

Example 12: Preparation of Ribociclib Phosphate

Under inert atmosphere, a solution of phosphoric acid (1.6 g) in water (9 mL) was added at 20° C. to ribociclib base (3.0 g). The suspension was kept under stirring for 15 min at 20° C. No complete dissolution was achieved. The suspension was heated to 45° C. and water (3.0 mL) was added. A cloudy solution was observed, to which acetone (60 mL) was added dropwise in 10 min. The suspension was cooled down to 0° C. in 1 h, then kept under stirring at 0° C. for 1 h. Ribociclib phosphate was isolated by filtration, washed with acetone (6 mL) and dried under vacuum at 50° C. for 18 h. Ribociclib phosphate was obtained as a solid (3.5 g, 95.1% yield).

Example 13: Preparation of Ribociclib Malate

Procedure A

Under inert atmosphere, ribociclib base (3.0 g) was suspended in i-PrOH (60 mL) and the suspension was heated to 80° C. As no complete dissolution was achieved, further i-PrOH was added (72 mL) and temperature was increased to 84° C. The resulting cloudy solution was filtrated on a dicalite pad. DL-malic acid (1.9 g) in i-PrOH (18.5 mL), previously prepared at 50° C., was added to the Ribociclib solution. Solid formation was observed at the end of addition. The suspension was cooled down to 15° C. in 1.5 h, then kept under stirring at 15° C. for 1 h. Ribociclib malate was isolated by filtration, washed with i-PrOH (6 mL) and dried under vacuum at 50° C. for 18 h. Ribociclib malate was obtained as a solid (2.9 g, 73.8% yield).

Procedure B

Under inert atmosphere, a solution of DL-malic acid (1.9 g) in water (9 mL) was added at 20° C. to ribociclib base (3.0 g). The suspension was kept under stirring for 20 min at 20° C., achieving complete dissolution. Acetone (60 mL) was added dropwise in 10 min to the Ribociclib solution. The suspension was kept under stirring at 20° C. for 1 h, then cooled down to −5° C. in 45 min and kept under stirring at −5° C. for 1 h. Ribociclib malate was isolated by filtration, washed with acetone (6 mL) and dried under vacuum for 72 h. Ribociclib malate was obtained as a solid (3.1 g, 78.9% yield).

Example 14: Preparation of Ribociclib Maleate

Under inert atmosphere, a solution of maleic acid (1.6 g) in water (9 mL) was added at 20° C. to ribociclib base (3.0 g). The suspension was kept under stirring for 15 min at 20° C., achieving complete dissolution. Acetone (60 mL) was added dropwise in 10 min to the Ribociclib solution. The mixture was cooled down to −5° C. in 45 min. The resulting suspension was diluted with further acetone (30 mL), then kept under stirring at −5° C. for 1 h. Ribociclib maleate was isolated by filtration, washed with acetone (6 mL) and dried under vacuum at 50° C. for 18 h. Ribociclib maleate was obtained as a solid (1.3 g, 34.0% yield).

Example 15: Preparation of Form B of Ribociclib Succinate

Procedure A

Succinic acid (4.35 g, 8 eq) was dissolved in water (8 mL) at 85° C. under inert conditions; Ribociclib base (2 g, 1 eq) was then added obtaining a complete dissolution at 85° C. This solution was quickly poured (about 1 minute) in a reactor containing acetone (50 mL, 25 v/w) at 10° C. After about 10 minutes the crystallization occurred. The suspension was heated to 45° C. and left under stirring at this temperature for 16 hours observing complete dissolution. The solution was cooled down to 10° C. and the resulting suspension was filtered after about 24 hours. Solid was dried under vacuum at 60° C. for about 16 hours. The material was analyzed by XRPD and identified as form C of ribociclib succinate.

100 mg of Ribociclib succinate Form C was placed in 100% RH chamber for 3 days at room temperature. The material was analyzed by XRPD and identified as form B of ribociclib succinate.

Procedure B 1 g of non-hydrated Ribociclib succinate prepared according to reference example 2 was milled in ball mill for 60 minutes, at room temperature, at a frequency of 25 s−1 to afford amorphous ribociclib succinate.

100 mg of the amorphous ribociclib succinate was placed in 100% RH chamber for 7 days at room temperature. The obtained material was analyzed by XRPD and identified as form B of ribociclib succinate.

Procedure C

In a 2 L reactor, Ribociclib base (30 g) was dissolved in i-PrOH (1 L) at 80° C. The solution was then cooled to 70° C., filtered on a dicalite pad and heated again to 80° C. In the meanwhile, succinic acid (8.56 g, 1.05 eq.) was dissolved in i-PrOH (240 ml) at 60° C. and the solution was filtered on a dicalite pad. The solution of succinic acid was then added to the previously prepared solution of Ribociclib at 80° C. in around 30 minutes and the resulting solution was seeded with non-hydrated Ribociclib succinate prepared according to reference example 2 (0.6 g, 2%) (NB seeding step is optional).

The mixture was then cooled down to 20° C. in 1 h and kept under stirring at this temperature for 1 h.

The obtained solid was isolated by filtration, washed with i-PrOH (90 ml) and dried under vacuum in oven at 60° C. for 16 h to afford non-hydrated Ribociclib succinate (36.5 g, 99.94% of purity and 94% yield). 100 mg of non-hydrated Ribociclib succinate, produced as described above, was placed in 100% RH chamber for 7 days at room temperature. The obtained material was analyzed by XRPD and identified as form B of ribociclib succinate.

Procedure D 300 mg of non-hydrated Ribociclib succinate prepared as described in procedure C was slurried in 0.5 ml of mixture of water and ethanol (ratio 1:1) at room temperature for 21 hours, 250 rpm. The obtained material was was dried under N2 atmosphere for 3 hours and then analyzed by XRPD and identified as form B of ribociclib succinate.

Example 16: Single Crystal Data for Form B of Ribociclib Succinate

Crystals of form B of Ribociclib succinate were obtained as following: 300 mg of Ribociclib succinate (Form C) was placed in 100% RH chamber for 5 days at room temperature. The material was analyzed by XRPD and identified as form B of Ribociclib succinate.

Synchrotron Data Measurement

The sample was placed in the 0.9 mm capillary made from non-diffracting glass no. 50 (Hilgenberg). Powder diffraction pattern was measured using synchrotron radiation at wavelength 0.354339(3) Å.

Structure Solution and Refinement

The reflection position was determined in DASH and Expo2014 software. Indexation was done in DICVOLO6 software (DASH peak positions) and N-TREOR (Expo2014 positions). Only one small peek (d=6.7926 Å) was not indexed (impurity expected). Both indexation software offered identical solution in triclinic system.

Structure was solved in DASH software by simulated annealing. The model of ribociclib molecule was created by QM DTF calculation (DMOL3 software). The succinic acid molecule shape was taken from CSD database (structure code SUCACB02). The space group P-1 was determined based on following information: the triclinic system, 2 molecules in unit cell as calculated from expected molecular volume and information from ss-NMR confirming only 1 molecule in asymmetric unit cell. The solution was thus problem with 21 DOF (degrees of freedom) level, 12 DOF for ribociclib and 9 DOF for succinic acid. 200 DASH runs had given 36 identical solutions with acceptable χ factor.

The DASH solution was refined in Jana software. Residual electron density map indicate the presence of 2 water molecules per 1 Ribociclib succinate in the structure. The water molecules create a H-bridge network giving sense—so it is highly probable the structure is a dihydrate. Hydrogen atoms were placed in position determined from geometry or positions expected from the H-bond system. The positions of water hydrogen's are not known.

Unit Cell Parameters for Ribociclib Succinate, Form B

| | |
|---|---|
| cell_length_a | 13.88025(13) Å |
| cell_length_b | 12.79118(18) Å |
| cell_length_c | 8.88873(8) Å |
| cell_angle_alpha | 67.9314(12)o |
| cell_angle_beta | 98.1568(13)o |
| cell_angle_gamma | 96.1246(12)o |
| cell_volume | 1445.28(3) Å3 |
| cell_measurement_temperature, | 293 K |
| symmetry_cell_setting | triclinic |
| symmetry_space_group_name_H-M | 'P -1' |

The invention claimed is:

1. A crystalline form of Ribociclib succinate designated form B, characterized by data selected from one or more of the following:
   (i) an X-ray powder diffraction pattern having peaks at 6.5, 7.5, 10.2, 10.9 and 12.0 degrees two theta±0.2 degrees two theta;
   (ii) an X-ray powder diffraction pattern having peaks at 6.5, 7.5, 10.2, 10.9 and 12.0 degrees two theta±0.2 degrees two theta and also having any one, two, three, four or five additional peaks selected from 14.6, 20.2, 20.7, 25.4 and 26.6 degrees two theta±0.2 degrees two theta;
   (iii) an X-ray powder diffraction pattern substantially as depicted in FIG. 2;
   (iv) a solid state $^{13}$C NMR spectrum having peaks at 183.0, 165.5, 156.5, 138.3 and 103.1 ppm±0.2 ppm;
   (v) a solid state $^{13}$C NMR spectrum having the following chemical shift absolute differences between said characteristic peaks at 183.0, 165.5, 156.5, 138.3 and 103.1 ppm±0.2 ppm and a reference peak at 122.3 ppm±1 ppm of 60.7, 43.2, 34.1, 15.9 and (−19.2)±0.1 ppm; or
   (vi) a solid state $^{13}$C NMR spectrum substantially as depicted in FIG. 12 or substantially as depicted in FIG. 13;
   (vii) an FT-IR spectrum having absorptions at 1605, 1525, 1399, 1261 and 786 cm−1±4 cm−1;
   (viii) an FT-IR spectrum substantially as depicted in FIG. 8 or substantially as depicted in FIG. 9.

2. The crystalline form B according to claim 1 wherein crystalline form is isolated, or wherein the crystalline form is substantially free of any other solid state forms.

3. A process for preparing crystalline form B of ribociclib succinate comprising:
 a) providing ribociclib succinate in a solvent system comprising water and ethanol; b) optionally heating; c) optionally cooling; d) optionally seeding with form B seeds and e) isolating crystalline from B.

4. The process according to claim 3 wherein the process is performed with stirring.

5. The process according to claim 3 wherein the ribociclib succinate used in step a) is non-hydrated ribociclib succinate.

6. The process according to claim 3 wherein the solvent system in step a) consists of ethanol and water.

7. The process according to claim 3 wherein in step a) a slurry is formed.

8. The process according to claim 3 wherein the ethanol-water ratio is about 1:1.

9. Crystalline form B of ribociclib succinate produced by the process according to claim 3.

10. A process according to claim 3 wherein the crystalline form B of ribociclib succinate is combined with a pharmaceutically acceptable excipient to produce a pharmaceutical composition.

11. Use of crystalline form B of ribociclib succinate according to claim 1 in the preparation of other solid state forms of ribociclib succinate, ribociclib and/or other salts of ribociclib.

12. Use of crystalline form B of ribociclib succinate according to claim 1 in the preparation of a pharmaceutical composition or a formulation comprising ribociclib succinate.

13. Crystalline form B of ribociclib succinate according to claim 1 for use in the preparation of other solid state forms of ribociclib succinate, ribociclib and/or other salts or ribociclib.

14. Crystalline form B of ribociclib succinate according to claim 1 for use in the preparation of a pharmaceutical composition or a formulation comprising ribociclib succinate.

15. A pharmaceutical composition comprising crystalline form B of ribociclib succinate according to claim 1.

16. A process for preparation of a pharmaceutical composition according to claim 15 comprising combining form B of ribociclib succinate and at least one pharmaceutically acceptable excipient.

17. A pharmaceutical composition produced by the process of claim 16.

18. A pharmaceutical composition according to claim 15 for use as a medicament.

19. A method of treating breast cancer comprising administering a therapeutically effective amount of form B of Ribociclib succinate according to claim 1, or a pharmaceutical composition or formulation comprising thereof, to a subject suffering breast cancer, or otherwise in need of the treatment.

* * * * *